(12) United States Patent
Belongia et al.

(10) Patent No.: US 8,090,244 B2
(45) Date of Patent: Jan. 3, 2012

(54) VOLATILE MATERIAL DISPENSER

(75) Inventors: David C. Belongia, Burlington, WI (US); James R. Crapser, Racine, WI (US); Thomas A. Helf, New Berlin, WI (US); Scott D. Walter, Twin Lakes, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 573 days.

(21) Appl. No.: 12/319,613

(22) Filed: Jan. 9, 2009

(65) Prior Publication Data

US 2010/0176213 A1    Jul. 15, 2010

(51) Int. Cl.
*A61H 33/12* (2006.01)

(52) U.S. Cl. .................. 392/403; 392/386; 392/406

(58) Field of Classification Search ........... 392/386–406
See application file for complete search history.

(56) References Cited

U.S. PATENT DOCUMENTS

| | | | |
|---|---|---|---|
| 5,148,938 A | 9/1992 | Morgan, Jr. |
| 5,304,358 A | 4/1994 | Hoyt et al. |
| 5,361,522 A | 11/1994 | Green |
| 5,661,635 A | 8/1997 | Huffman et al. |
| 5,887,118 A | 3/1999 | Huffman et al. |
| 6,021,254 A | 2/2000 | Hunter |
| 6,104,866 A | 8/2000 | DeWitt et al. |
| 6,169,595 B1 | 1/2001 | Manne |
| 6,554,203 B2 | 4/2003 | Hess et al. |
| 6,602,475 B1 | 8/2003 | Chiao |
| 6,609,935 B2 | 8/2003 | Huang |
| 7,082,259 B2 | 7/2006 | Zobele |
| 7,143,766 B2 | 12/2006 | Schuster et al. |
| 7,200,363 B2 | 4/2007 | Greco et al. |
| 7,203,417 B2 | 4/2007 | Manne |
| 2003/0206834 A1 | 11/2003 | Chiao et al. |
| 2004/0204043 A1 | 10/2004 | Wang et al. |
| 2004/0235430 A1 | 11/2004 | Ma et al. |
| 2005/0013728 A1 | 1/2005 | Huang |
| 2005/0244307 A1 | 11/2005 | Gygax et al. |
| 2006/0193610 A1 | 8/2006 | Han |
| 2006/0258215 A1 | 11/2006 | Lai et al. |
| 2007/0148053 A1 | 6/2007 | Tian |
| 2007/0166575 A1 | 7/2007 | McLeod |
| 2007/0206154 A1 | 9/2007 | Brady |
| 2007/0243791 A1 | 10/2007 | Stedman |
| 2007/0299298 A1 | 12/2007 | Suissa et al. |
| 2008/0095522 A1 | 4/2008 | Deflorian et al. |
| 2008/0143890 A1 | 6/2008 | Rosencwaig et al. |
| 2008/0179424 A1 | 7/2008 | Cheung |
| 2008/0199639 A1 | 8/2008 | Mock |
| 2009/0047652 A1 | 2/2009 | Spector |
| 2009/0093282 A1 | 4/2009 | Hwang et al. |

FOREIGN PATENT DOCUMENTS

| | | |
|---|---|---|
| CN | 1734388 | 2/2006 |
| JP | 2006-155565 | 6/2006 |
| JP | 2006-221246 | 8/2006 |
| WO | WO 2007/082411 | 7/2007 |
| WO | WO 2007/137483 | 12/2007 |

*Primary Examiner* — Thor Campbell (57) ABSTRACT

A volatile material dispenser includes an upper housing with an opening extending therethrough and a lower housing with an opening extending therethrough, wherein the upper housing is secured to the lower housing to define a cavity therebetween. Electrical circuitry is disposed within the cavity, wherein the electrical circuitry includes a heater and a USB interface that extends from the upper and lower housings. Further, a volatile material cartridge is disposed within the cavity. The dispenser is adapted to dispense volatile material from the volatile material cartridge through the openings in the upper and lower housings in a passive mode and an active mode, wherein the USB interface is coupled to a power source to energize the heater in the active mode.

6 Claims, 10 Drawing Sheets

VOLATILE MATERIAL DISPENSER

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure relates generally to volatile material dispensers, and more particularly, volatile material dispensers that are adapted to operate in active and passive modes.

2. Description of the Background of the Invention

Volatile material dispensers are used to diffuse or disperse volatile materials, such as perfumes, deodorizers, insecticides, insect repellants, and the like. Many such devices are passive devices that require only ambient air flow to disperse the volatile material throughout a space, while other devices are active devices. Active devices are found in a variety of forms, some include fans and/or heaters to aid in the dispersal of volatile materials, others actuate a valve stem of an aerosol container to dispense a volatile material contained therein, still others utilize an ultrasonic transducer to break up a liquid volatile material into droplets that are ejected from the device, and yet others include combinations of the above or any other known type of active device.

Generally, volatile material dispensers are specifically designed to function optimally as either a passive device or an active device. For example, an active device requires a power source, such as from a battery or by plugging the device into a power outlet, while a passive device does not. Further, an active device requires additional components to actively disperse the volatile material, such as, a heater, a fan, a motor, an electronic controller, and other electrical components. Consequently, passive devices are generally designed to be smaller devices that can be placed in a room inconspicuously, while active devices are typically larger, in part, because of the additional components that are required. However, in either case of an active or a passive diffusion device, such devices are generally intended for use in a stationary position on top of a support structure or perhaps plugged into a power outlet.

Consequently, there is a need for a volatile material dispenser that is specifically designed to operate in both active and passive modes.

SUMMARY OF THE INVENTION

According to one embodiment, a volatile material dispenser includes an upper housing with an opening extending therethrough and a lower housing with an opening extending therethrough, wherein the upper housing is secured to the lower housing to define a cavity therebetween. Electrical circuitry is disposed within the cavity, wherein the electrical circuitry includes a heater and a USB interface that extends from the upper and lower housings. Further, a volatile material cartridge is disposed within the cavity. The dispenser is adapted to dispense volatile material from the volatile material cartridge through the openings in the upper and lower housings in a passive mode and an active mode, wherein the USB interface is coupled to a power source to energize the heater in the active mode.

According to another embodiment, a volatile material dispenser includes an upper housing secured to a lower housing to define a cavity therebetween, wherein an opening is provided through one of the upper and lower housings. Electrical circuitry is disposed within the cavity, wherein the electrical circuitry includes a heater and an electrical connection that is adapted to be coupled to a power source to energize the heater. Further, a volatile material cartridge is disposed within the cavity, wherein the volatile material cartridge is formed from a permeable membrane that defines a compartment within which a volatile material is contained.

According to yet another embodiment, a volatile material dispenser includes an upper housing secured to a lower housing to define a cavity therebetween, wherein an opening is provided through one of the upper and lower housings. Electrical circuitry is disposed within the cavity, wherein the electrical circuitry includes a heater and an electrical connection that is adapted to be coupled to a power source to energize the heater. Further, a guidance feature is disposed on one or both of the upper or lower housings to orient the dispenser so that it is coupled properly to a power source. The dispenser is adapted to dispense volatile material in a passive mode and an active mode, wherein the electrical connection is coupled to a power source to energize the heater in the active mode, Other aspects and advantages of the present invention will become apparent upon consideration of the following detailed description.

DETAILED DESCRIPTION OF THE DRAWINGS

Figure 1:
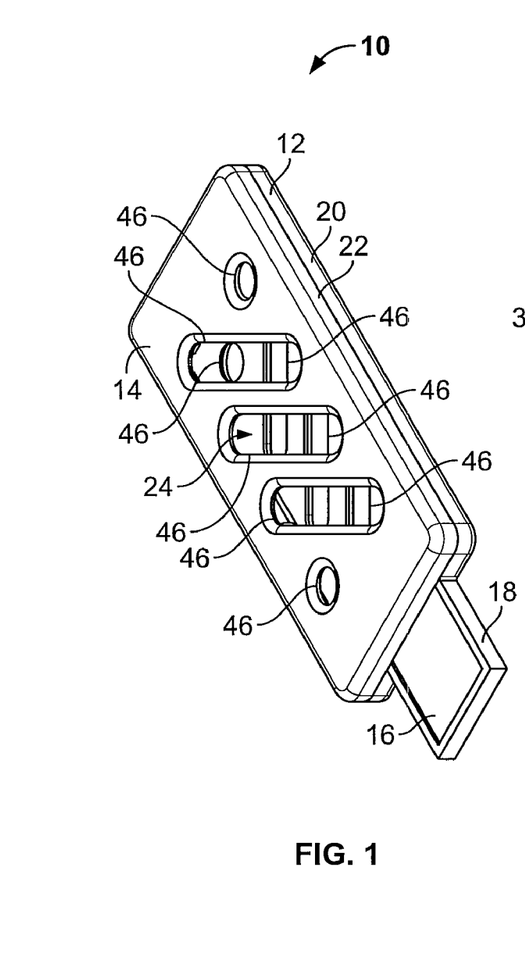
FIG. 1 is an isometric view of a dispenser according to one embodiment.
Figures 2, 3:
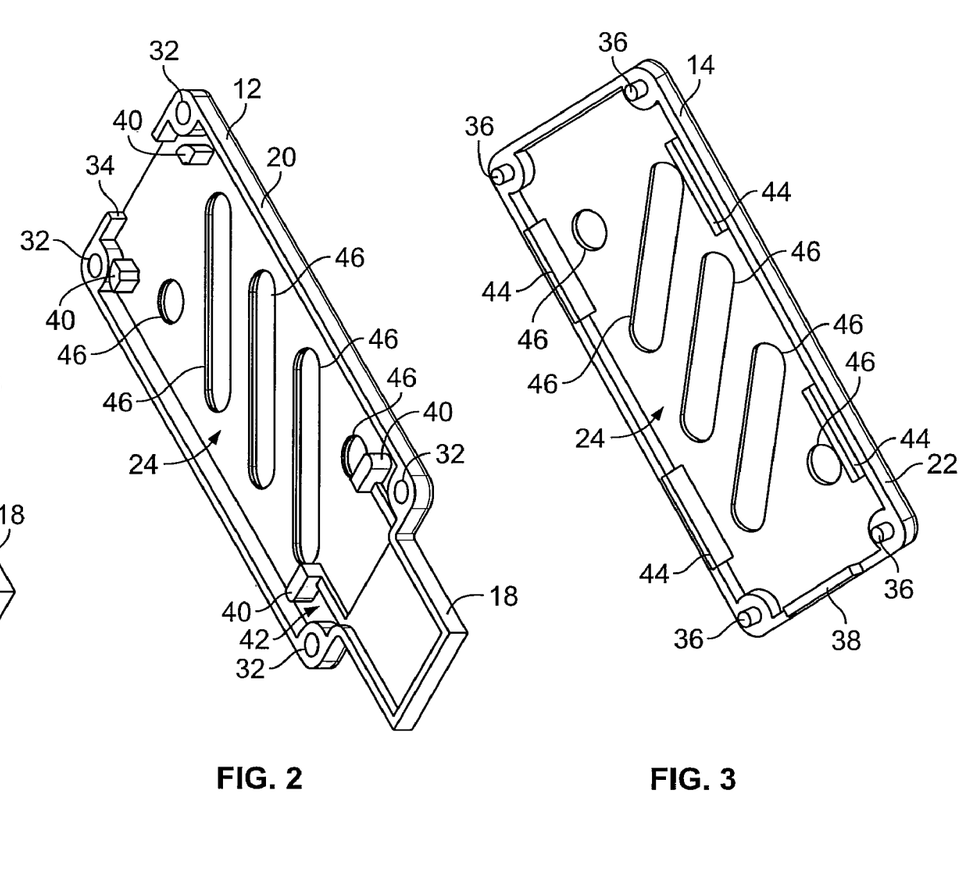
FIG. 2 is an isometric view of a lower housing of the dispenser of FIG. 1.
FIG. 3 is an isometric view of an upper housing of the dispenser of FIG. 1.

FIGS. 1-4 illustrate generally a fragrance dispenser 10 that includes a lower housing 12, an upper housing 14, and an electrical connection 16. Referring to FIG. 2, the lower housing 12 is generally rectangular and includes a rectangular protrusion 18 that extends from a side of the lower housing 12 so that the housing 12 resembles the size and shape of a Universal Serial Bus ("USB") flash memory drive, as would be apparent to one of ordinary skill in the art. The upper housing 14 is also generally rectangular and corresponds generally to the size of the lower housing 12. However, in other embodiments, the dispenser 10 can be any other size or shape, such as, square, circular, triangular, or any other geometric or abstract shape. The rectangular protrusion 18 on the lower housing 12 supports at least a portion of the electrical connection 16, which in the present embodiment, is a USB interface. Further, the lower housing 12 includes a wall 20 that extends from an inner surface thereof around a periphery of the lower housing 12. Similarly, the upper housing 14 includes a wall 22 that extends from an inner surface thereof around a periphery of the upper housing 14. In FIG. 1, the walls 20, 22 of the lower and upper housings 12, 14, respectively, are secured together to form a cavity 24 therebetween. The cavity 24 is configured to receive a volatile material cartridge 26 and electrical circuitry 30 (see FIGS. 4 and 5, for example).

Referring more specifically to FIG. 2, the wall 20 of the lower housing 12 defines a plurality of circular openings 32 that are located proximate corners of the lower housing 12. In addition, there is a break 34 in the wall 20 such that the wall 20 does not extend continuously around the entire periphery of the lower housing 12. In FIG. 3, a plurality of circular pins 36 that correspond to the positions of the circular openings 32 extend from the wall 22 of the upper housing 14. Further, the wall 22 of the upper housing 14 includes a projection 38 that corresponds to the break 34 in the wall 20 of the lower housing 12. In the present example, four pins 36 interact with four holes 32 to secure the lower and upper housings 12, 14 together. However, any number of pins and holes can be utilized or the pins and holes can be omitted altogether as would be apparent to one of ordinary skill in the art. Further, in other examples, the lower and upper housings 12, 14 can be secured together in other known ways, for example, by welds, adhesives, screws, nuts and bolts, clips, and the like.

The lower housing 12 also includes a plurality of posts 40 that are spaced inwardly from the wall 20 and are located proximate the openings 32. In the present example, the plurality of posts 40 defines a channel 42 that receives the electrical circuitry 30. Further, the upper housing 14 includes a plurality of ribs or flanges 44 that extend from an inner face of the housing and are disposed adjacent the wall 22. The ribs 44 further secure the electrical circuitry 30 within the channel 42 when the lower and upper housings 12, 14 are secured together. Another feature of the dispenser 10 is a plurality of openings 46 that extend through each of the upper and lower housings 12, 14. In the dispenser 10 of FIGS. 1-4, each of the lower and upper housings 12, 14 includes two circular openings and three elongate openings. However, in other examples, the openings 46 through the lower and upper housings 12, 14 can be of any shape and number. Further, the openings 46 can extend through only one of the upper and lower housings 12, 14.

Figure 4:
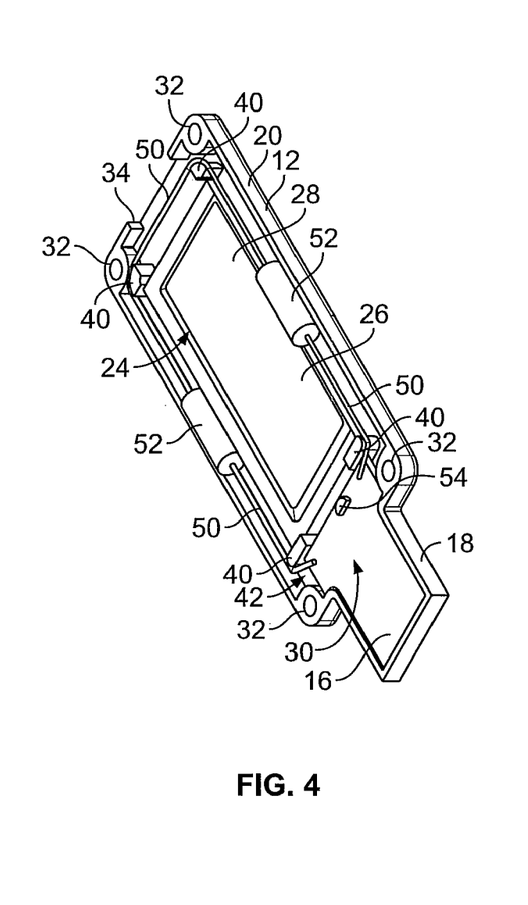
FIG. 4 is an isometric view of the lower housing of the dispenser of FIG. 1 with electrical circuitry and a volatile material cartridge.

FIG. 4 illustrates an example of the volatile material cartridge 26 that is formed from a non-porous permeable membrane that is folded over on itself and sealed along three sides to form a compartment within which a volatile material 28 is contained. The permeable membrane is comprised of a co-extrusion of polypropylene ("PP") and low density polyethylene ("LDPE") and is clear and/or translucent, allowing for visibility of the volatile material 28 contained therein. In other embodiments, the permeable membrane can be opaque, as shown in FIG. 4 for purposes of clarity. In another example, a seal (not shown) can be disposed within the dispenser 10 to prevent fluid exchange between the volatile material cartridge 26 and the electrical connection 16.

Figure 5:
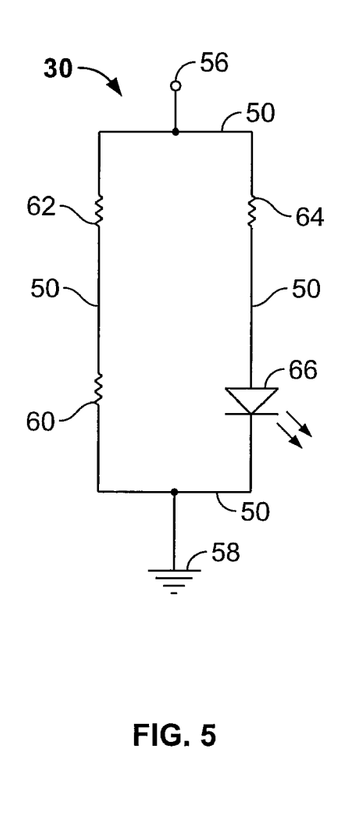
FIG. 5 is an electrical schematic of the electrical circuitry of the dispenser of FIG. 1, according to one example.

FIGS. 4 and 5 also show the electrical circuitry 30, which includes the electrical connection 16, for example, a USB interface, through which the dispenser 10 receives power. The electrical connection 16 is disposed within the rectangular protrusion 18 of the lower housing 12 to protect the electrical connection 16. Further, the electrical connection 16 is coupled via conductors 50 to one or more heating elements 52. In FIG. 4, the dispenser includes two heating elements 52 that are positioned on opposite sides of the volatile material cartridge 26 to apply heat evenly to the cartridge 26 when the heating elements 52 are energized. However, in other embodiments, fewer or additional heating elements 52 can be placed around the cartridge 26 in any configuration, as would be apparent to one of skill in the art to provide better heat distribution and to eliminate hot spots. Additional electrical components can also be coupled to the electrical connection 16, for example, a light source 54. In FIG. 5, the electrical circuitry 50 includes a voltage supply terminal 56 and a ground terminal 58. First and second resistors 60, 62, respectively, are coupled in parallel with a third resistor 64 and a light emitting diode ("LED") 66. The first and second resistors 60, 62 function as heating elements 52 and the third resistor 64 is a current limiting resistor for the LED 66, which functions as the light source 54.

Figure 6:
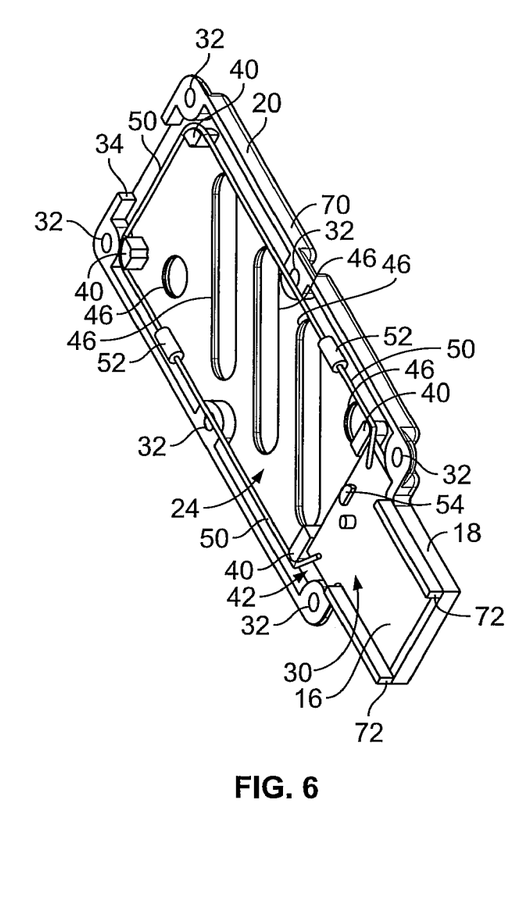
FIG. 6 is an isometric view of a lower housing of a dispenser similar to the one shown in FIG. 2 according to another embodiment.

FIG. 6 illustrates another embodiment of a lower housing 70 that is similar to the lower housing 12 of FIGS. 1, 2, and 4, wherein like numerals are used to designate similar structures. The lower housing 70 is also generally rectangular and includes the rectangular protrusion 18 so that the lower housing 70 resembles the size and shape of a USB flash memory drive. Further, the lower housing 70 includes the wall 20 that defines a plurality of openings 32. Unlike the lower housing 10, the lower housing 70 includes six openings 32 that interact with six pins in an upper housing (not shown). In addition, the lower housing 70 of FIG. 6 includes guide walls 72 that orient the fragrance dispenser 10 so that it is inserted properly into a power source, e.g., a USB port. In yet an alternative embodiment, the guide walls 72 can be included in the upper housing (not shown) or in both the upper and lower housings.

Alternatively or in conjunction, the electrical connection 16 can include suitable contacts on both sides thereof, so that the fragrance dispenser 10 can be inserted into a power source in any orientation. In such an embodiment, the rectangular protrusion 18 of the lower housing can be omitted or modified to expose contacts on both sides of the electrical connection 16.

The dispenser 10 can be made of any suitable material, for example, plastics, metals, ceramics, woods, etc. In one example, the dispenser 10 and the volatile material cartridge 28 are made from relatively inexpensive materials and are intended to be disposable after use. In another example, the dispenser 10 is intended to be reused by replacing an empty volatile material cartridge with a refill cartridge.

In use, the dispenser 10 can be operated in a passive mode or in an active mode. In the passive mode, the electrical connection 16 is not coupled to a power source and the volatile material is allowed to diffuse passively through the openings 46 to create a desired ambient effect. Such ambient effect can be a specific fragrance, deodorizer, insect repellant, etc., as would be known in the art. In one example, the dispenser 10 is a portable device that can be moved from room to room or carried by a user, for example, by being clipped to a belt or hung around a neck or wrist. In the active mode, the electrical connection 16 is coupled to a power source and the heating elements 52 generate heat to actively vaporize the volatile material 28 and disperse the vaporized material 28 through the openings 46 and into the environment. In the active mode, the light source 54 can also be energized to give a visual indication that the dispenser 10 is operating in the active mode. The volatile material cartridge 26 can be transparent or translucent so that the light from the light source 54 illuminates same and/or portions of the dispenser 10. In a more specific example, the electrical connection 16 is a USB interface and the dispenser 10 can be operated in a passive mode as described above and in an active mode where the dispenser is inserted into a USB port on a laptop, a television, or the like. In other examples, the electrical connection 16 can be adapted for coupling to an AC power outlet, a car cigarette lighter, a cell phone charger, a telephone jack, and the like. Further, the dispenser 10 can be used with adapters so that the dispenser 10 can be coupled to any type of power source.

Figure 7:
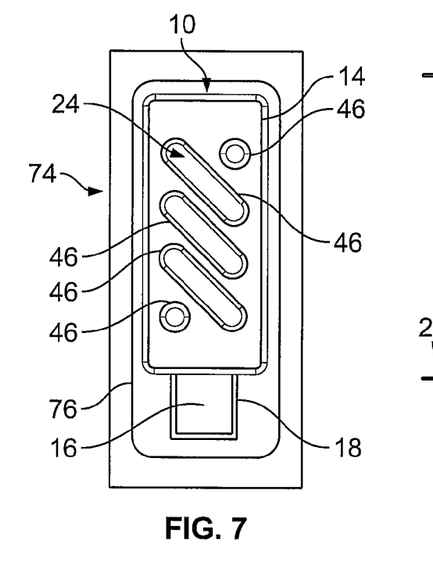
FIG. 7 is a plan view of the dispenser of FIG. 1 disposed within a container according to one embodiment.
Figure 8:
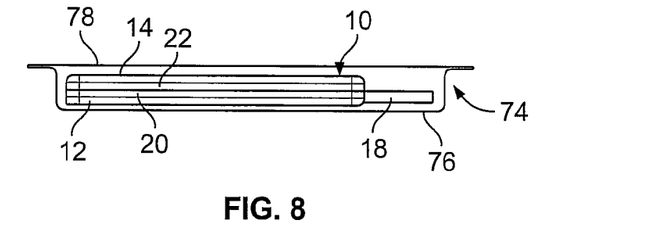
FIG. 8 is a diagrammatic side elevational view of the dispenser and the container of FIG. 7.
Figure 9:
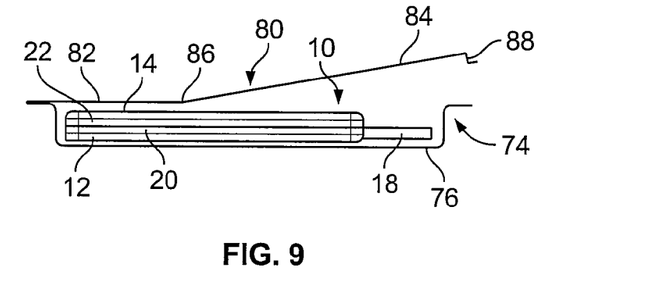
FIG. 9 is a diagrammatic side elevational view of the dispenser of FIG. 1 disposed within a container according to another embodiment.

Referring to FIGS. 7-9, the dispenser 10 can be housed in a container 74 before use to substantially prevent diffusion of the volatile material 28 into the environment. In one example, the container 74 includes a cup-shaped structure 76 formed from an impermeable material, such as a recycled polyethylene terephthalate ("RPET") layer adhesively bonded to a nylon laminate. The nylon laminate may also include a layer of ethylene vinyl acetate ("EVA") coextruded to each side of a middle nylon layer. The dispenser 10 is placed in the cup-shaped structure 76, which can be any general size and shape formed to accommodate the dispenser 10, and an impermeable laminate 78 is secured over the cup-shaped structure to prevent diffusion of the volatile material (see FIG. 8). The impermeable laminate 78 may include one or more layers of LDPE, aluminum foil, and/or polyester ("PET"). In the present embodiment, a layer of LDPE is bonded to one side of an aluminum foil layer and a layer of blended LDPE is adhesively bonded to the other side of the aluminum foil layer. Further, a PET layer is adhesively bonded to the LDPE layer. An extrusion bonding material may be used to bond the layers together. The polyester layer is generally suitable for printing and may be the outer surface of the impermeable laminate 78. Just before use, the impermeable laminate 78 is peeled from the container 74 and the dispenser 10 is removed to begin diffusing the volatile material 28 into the environment. Alternatively, the dispenser 10 may be removed from the container by merely pressing on the cup-shaped structure 76 to force the dispenser 10 through the impermeable laminate 78.

In another embodiment, the container 74 includes an impermeable cover 80 that is secured over the cup-shaped structure 76 and can be selectively opened and closed. The cover 80 can be made from the same or different material as the cup-shaped structure 76, as described above. Referring to FIG. 9, a first portion 82 of the cover 80 is fixedly secured to the cup-shaped structure 76 by a heat seal, weld, or adhesive, for example. Further, a second portion 84 of the cover 80 is attached to the first portion 82 via a hinge 86. The second portion 84 can be selectively opened and closed about the hinge 86 to allow for the insertion and removal of the dispenser 10. The present embodiment generally shows a snap-fit arrangement 88 for securing the second portion 84 to the cup-shaped structure 76. The snap-fit arrangement 88 can extend around a periphery of the second portion 84 to provide a continuous seal of the cover 80 to the cup-shaped structure 76. In other embodiments, the second portion 84 can be attached to the cup-shaped structure 76 in other known ways, for example, with a releasable or pressure sensitive adhesive. Consequently, the container 74 serves the dual purpose of providing a display case for the dispenser 10 and a carrying case so that the dispenser 10 can be selectively removed to diffuse the volatile material 28 contained therein and replaced to substantially prevent the diffusion of the volatile material 28. Other modifications can be made to the container 74 to still provide such dual functionality, for example, the cover 80 can be a single piece that is secured to the cup-shaped structure 76 with a releasable or pressure sensitive adhesive.

Figure 10:
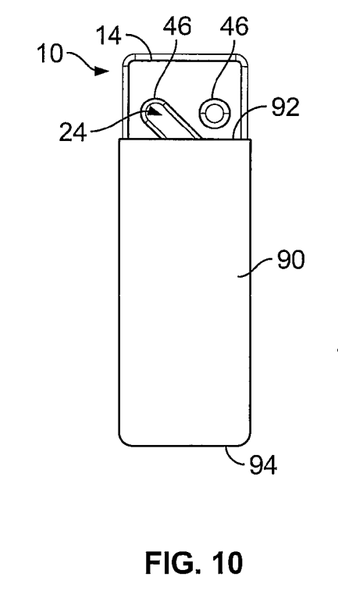
FIG. 10 is a plan view of the dispenser of FIG. 1 disposed within a sleeve according to one embodiment.
Figure 11:
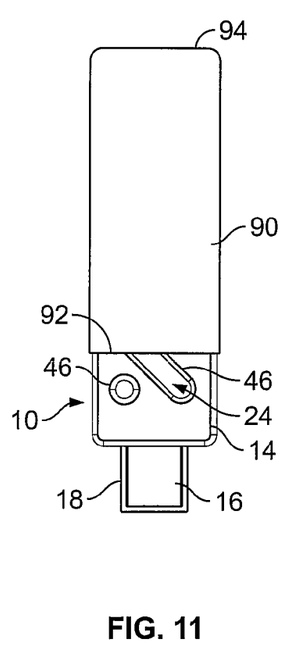
FIG. 11 is another plan view of the dispenser and the sleeve of FIG. 10.
Figure 12:
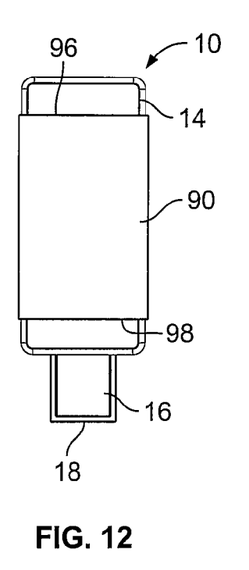
FIG. 12 is a plan view of the dispenser of FIG. 1 disposed within a sleeve according to another embodiment.

FIGS. 10-12 illustrate a sleeve 90 that is used with the dispenser 10 to protect the electrical connection 16 and/or to provide an intensity adjustment feature. In one example, the sleeve 90 is an elastomeric sleeve that has an open end 92 and a closed end 94. In FIG. 10, the electrical connection 16 of the dispenser 10 is inserted into the open end 92 of the sleeve 90 to protect same. In FIG. 11, the end opposite the electrical connection 16 is inserted into the open end 92 of the sleeve 90 and the sleeve 90 is moved with respect to the dispenser 10 to vary the exposure of the openings 46 to the environment and control the intensity of the diffusion of the volatile material 28 during operation in both active and passive modes. FIG. 12 illustrates another embodiment of the sleeve 90 that includes first and second open ends 96, 98, respectively. The sleeve 90 of FIG. 12 is slid over the electrical connection 16 to protect same and moved with respect to the openings 46 to control the intensity of the diffusion, as described above.

Figures 13, 14:
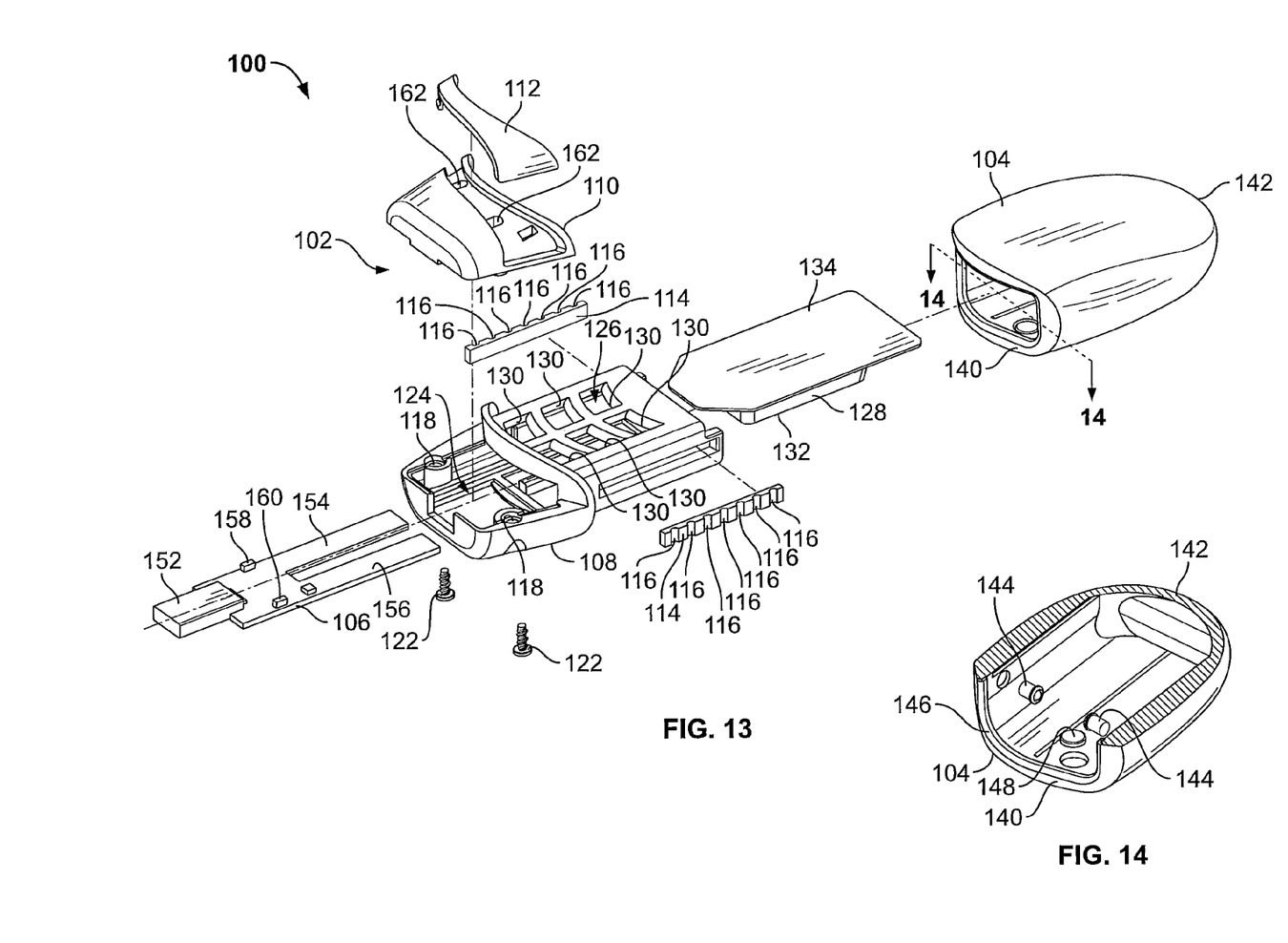
FIG. 13 is an exploded isometric view of a dispenser according to yet another embodiment.
FIG. 14 is a cross-sectional view taken generally along lines 14-14 of FIG. 13.

Referring now to FIGS. 13-20, another fragrance dispenser 100 includes a housing 102, a cover assembly 104, and a printed circuit board ("PCB") assembly 106. The housing 102 generally includes a housing base 108, a housing top 110, a lens 112, and one or more strips 114 that include lock detents 116. The housing base 108 includes screw holes 118 that extend therethrough. In addition, the housing top 110 includes screw holes 120 (see FIGS. 16 and 18, for example) that correspond to the screw holes 118 in the housing base 108. FIG. 13 illustrates screws 122 that are inserted through the screw holes 118, 120 in the housing base 108 and the housing top 110, respectively, to secure same together. However, in other examples, other means can be used to secure the housing 102, such as, welds, adhesive, clips, and the like. Further, the lens 112 is secured to the housing top 110 and the strips 114 are secured to the housing base 108. Any known means can be used to secure the lens 112 and the strips 114 to the housing 102, for example, an interference fit, welds, adhesive, clips, etc.

The housing base 108 also defines a slot 124 and a cavity 126. The slot 124 is adapted to receive the PCB assembly 106 (see FIG. 20, for example) and the cavity 126 is adapted to receive a replaceable volatile material cartridge 128 (see FIGS. 16 and 20, for example). The housing base 108 further defines a plurality of openings 130 above the cavity 126. In use, volatile material from the cartridge 128 diffuses through the openings 130 and into the environment. In one example, the volatile material cartridge 128 includes an impermeable cup-shaped structure 132 and a permeable membrane 134 over the cup-shaped structure 132 that acts as a sealed reservoir to contain a volatile material. The volatile material cartridge 128 may further include an impermeable laminate (not shown) that is adhered to the permeable membrane 134 to substantially prevent diffusion of the volatile material therethrough. In one example, the volatile material cartridge 128 is similar or identical to those described in U.S. Pat. No. 7,213,770, the disclosure of which is herein incorporated by reference in its entirety. In use, the impermeable laminate is pealed from the volatile material cartridge 128 and the cartridge is inserted into the cavity 126 with the cup-shaped structure 132 adjacent the PCB assembly 106 and the permeable membrane 134 adjacent the openings 130.

Figure 15:
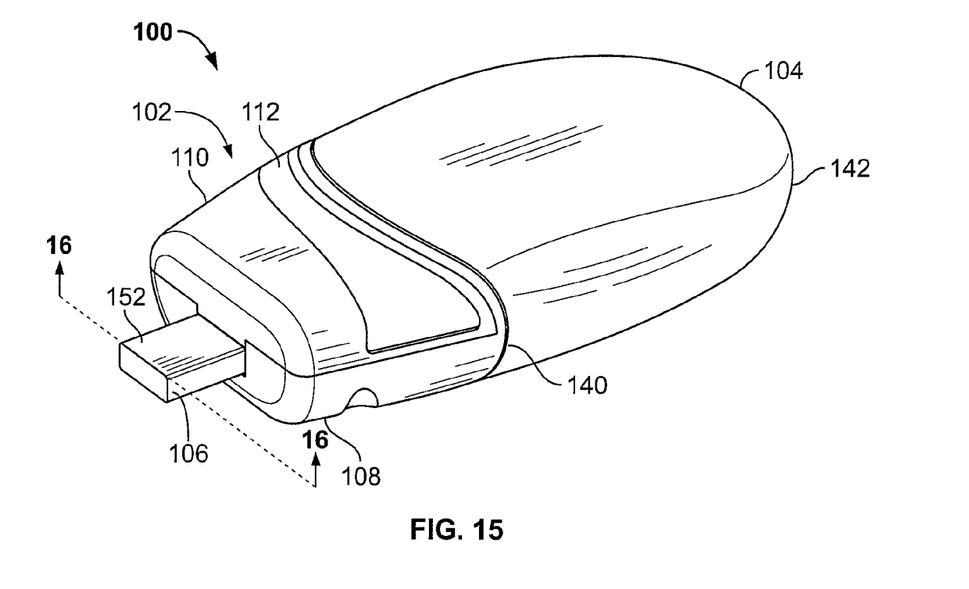
FIG. 15 is an isometric view of the dispenser of FIG. 13 in a closed position.
Figure 16:
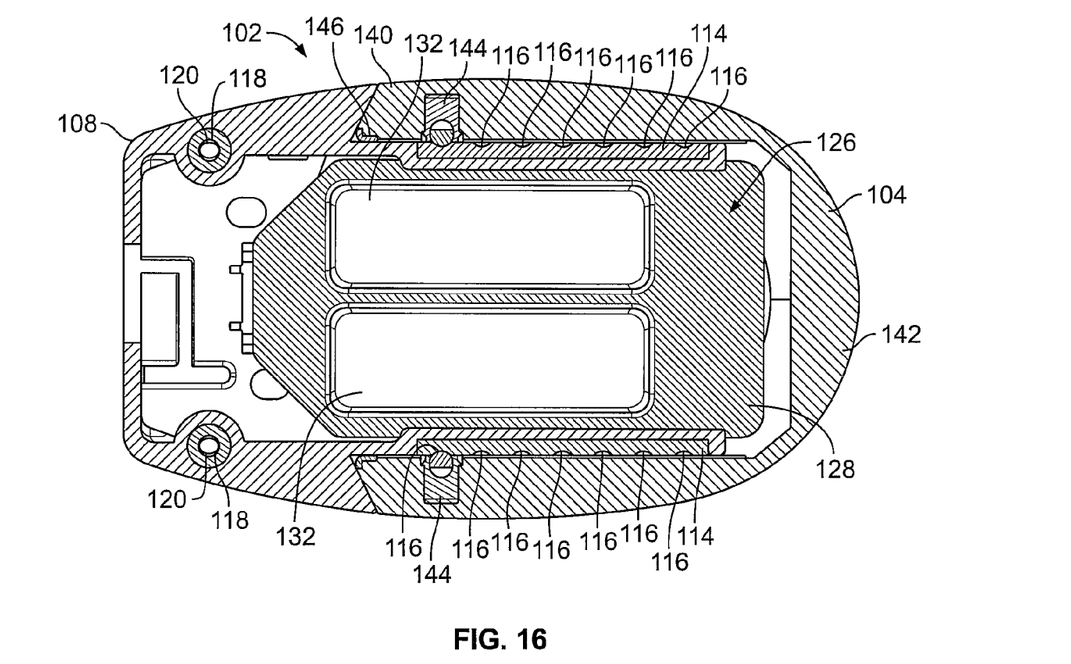
FIG. 16 is a cross-sectional view taken generally along lines 16-16 of FIG. 15.
Figure 17:
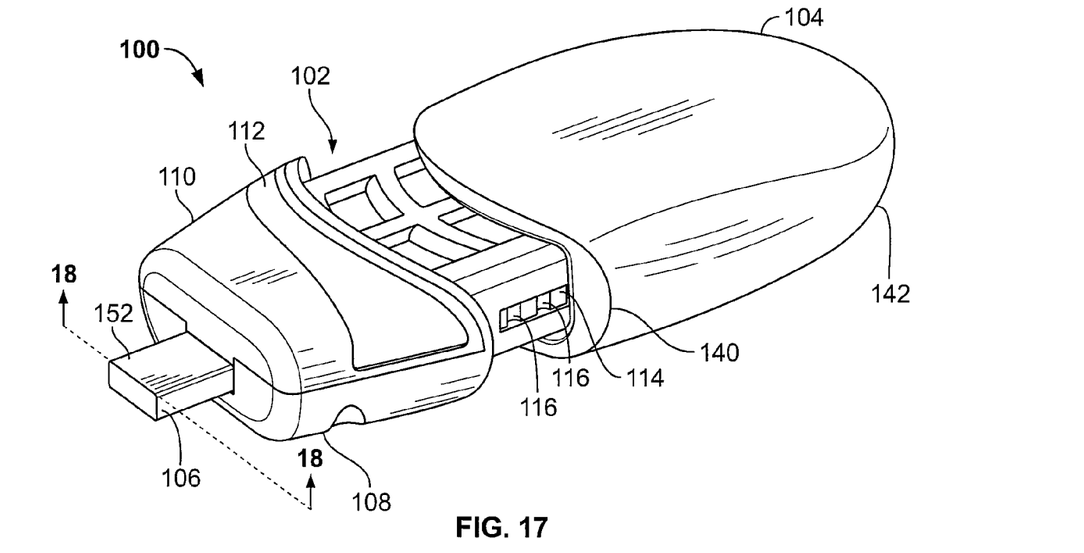
FIG. 17 is an isometric view of the dispenser of FIG. 13 in a partially open position.
Figure 18:
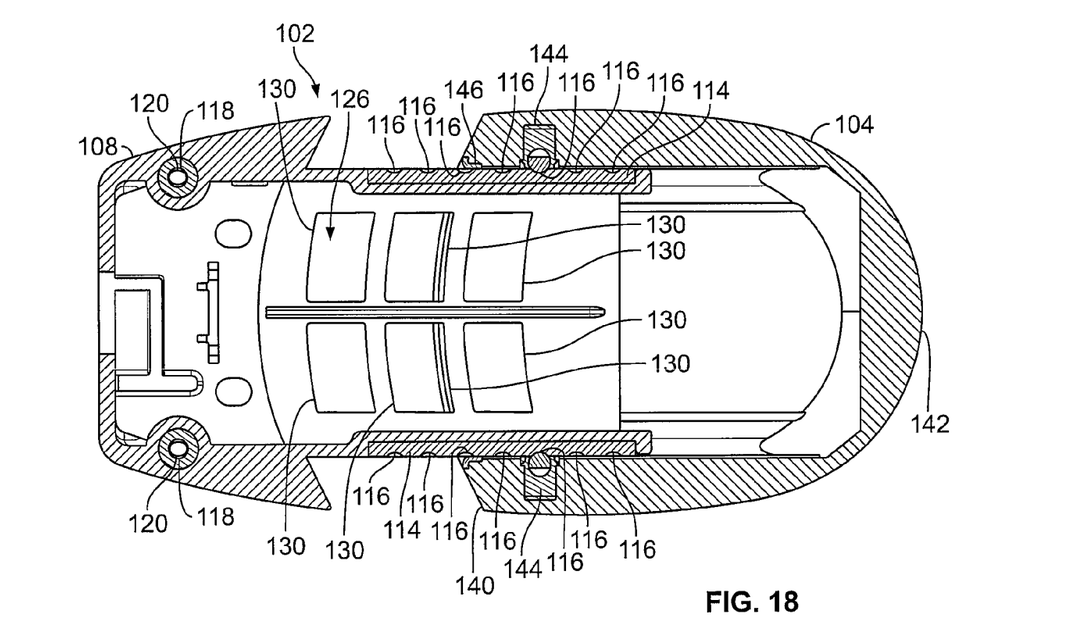
FIG. 18 is a cross-sectional view taken generally along lines 18-18 of FIG. 17 with a volatile material cartridge removed.
Figure 19:
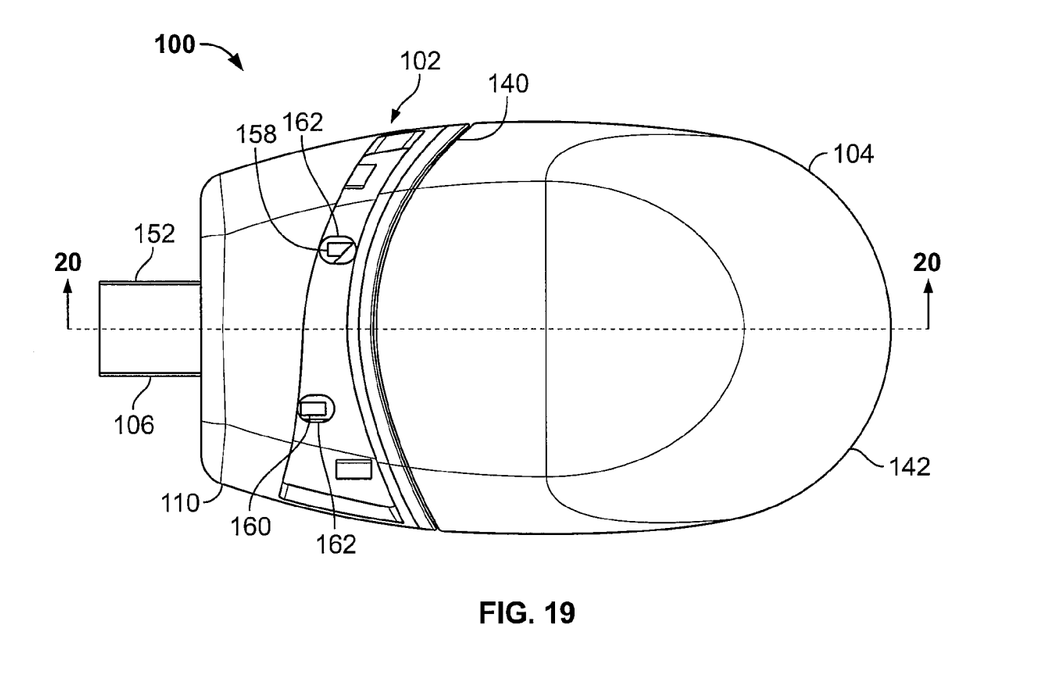
FIG. 19 is a plan view of the dispenser of FIG. 13.
Figure 20:
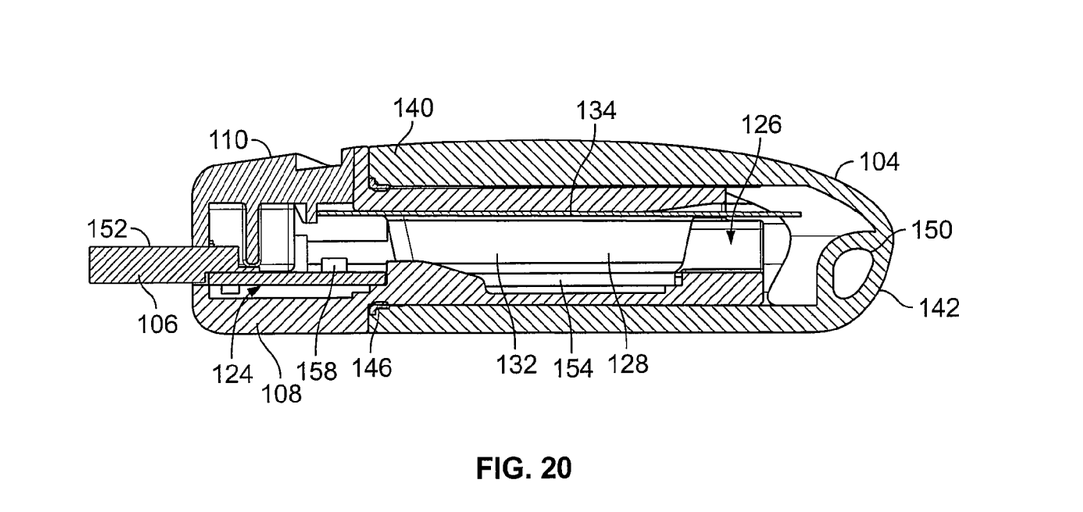
FIG. 20 is a cross-sectional view taken generally along lines 20-20 of FIG. 19.

The cover assembly 104 includes an open end 140 and a closed end 142. The housing 102 is inserted into the open end 140 to mount the cover assembly 104 over the housing 102. Referring to FIGS. 15 and 17, the cover assembly 104 is moved between a closed position and an open position to vary the exposure of the openings 130 to the environment and control the intensity of the diffusion of the volatile material. Referring to FIGS. 14, 16, and 18, the cover assembly 104 includes spring plungers 144 that engage the lock detents 116 to lock the cover assembly 104 into various positions with respect to the housing 102. The cover assembly 104 also includes a gasket 146 around the open end 140 that forms a seal with the housing 102 to substantially prevent diffusion of the volatile material to the environment when the dispenser 100 is in a closed position (see FIG. 15, for example). Further, the cover assembly 104 includes a magnet 148 proximate the open end, the function of which will be described in more detail hereinafter. Referring to FIG. 20, the cover assembly 104 also defines an aperture 150 proximate the closed end 142 through which a ring, clip, cord, chain, or the like can be inserted or secured so that the dispenser 100 can be attached to a support surface, such as, a door handle, hook, key chain, belt, or even around a body part of a user.

The PCB assembly 106 includes an electrical connection 152, for example, a USB interface, through which the dispenser 100 receives power. In the current example, the PCB assembly 106 also controls the operation of first and second heating elements 154, 156, respectively, and first and second LED's 158, 160, respectively. The housing top 110 further includes holes 162 that extend therethrough and correspond in position to the first and second LED's 158, 160, respectively.

In use, the dispenser 100 can be operated in a passive mode or in an active mode. In the passive mode, the electrical connection 152 is not coupled to a power source and the volatile material is allowed to diffuse passively through the openings 130 to create a desired ambient effect. The cover assembly 104 is moved with respect to the housing 102 to adjust the intensity of the volatile material that is dispersed into the environment. In the active mode, the electrical connection 152 is coupled to a power source and the heating elements 154, 156 are energized to heat and actively vaporize the volatile material within the cavity 126 and disperse the vaporized material through the openings 130 and into the environment. Further, the LED's 158, 160 can be energized when a respective heating element 154, 156 is energized to give a visual indication that the dispenser 100 is operating in the active mode. In the active mode, the cover assembly 104 is also moved to adjust the intensity of the volatile material that is dispersed to the environment. In addition, when the cover assembly 104 is in a closed position over the housing 102 (FIG. 15), magnetic fields from the magnet 148 interact with the PCB assembly 106 to turn off the dispenser 100. When the cover assembly 104 is moved into an open position (see FIG. 17), the magnetic fields from the magnet 148 no longer interact with the PCB assembly 106, which allows the dispenser 100 to be activated and operate as described above. In the present example, a magnetic switch is used to turn the dispenser 100 on and off in correspondence with the position of the cover assembly 104, however, in other embodiments, any other type of switch can be used, e.g., a mechanical switch or an electronic switch.

In one example, the electrical connection 152 is a USB interface, the volatile material cartridge includes first and second cup-shaped structures 132 (see FIG. 16, for example), and the PCB assembly 106 controls the first and second heating elements 154, 156 and the first and second LED's 158, 160. In the present example, the first and second compartments 132 can include the same or different volatile materials. Further, the PCB assembly 106 can energize the first and second heating elements 154, 156 alternatingly or concurrently and also can vary the time that each heating element 154, 156 is energized. By varying the control of the first and second heating elements 154, 156, user habituation to a volatile material can be minimized and a specific ambient effect can be created more effectively.

Figure 25:
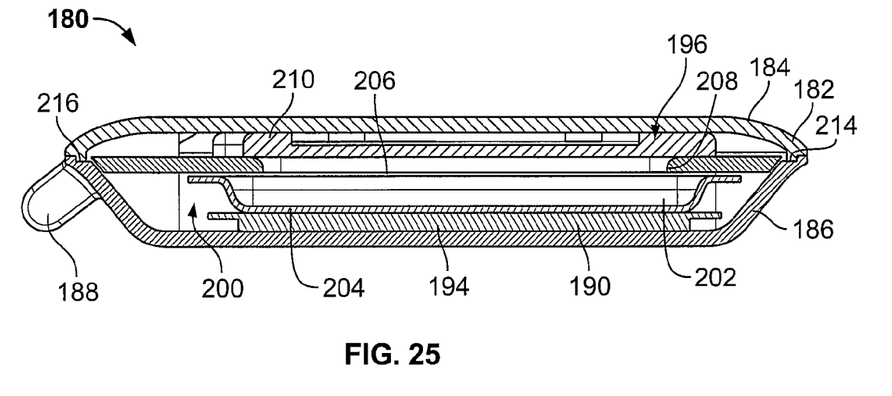
FIG. 25 is a cross-sectional view taken generally along lines 25-25 of FIG. 21.
Figure 26:
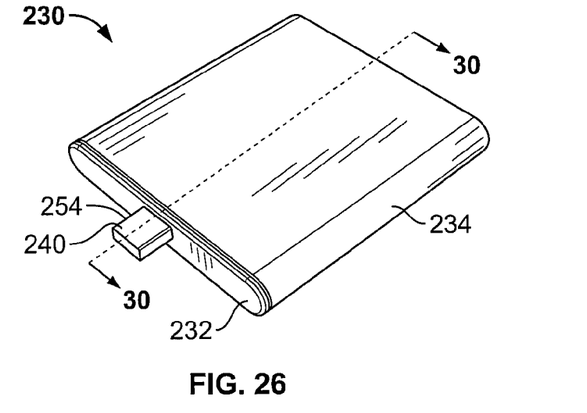
FIG. 26 is an isometric view of a dispenser according to a further embodiment in a closed position.
Figure 27:
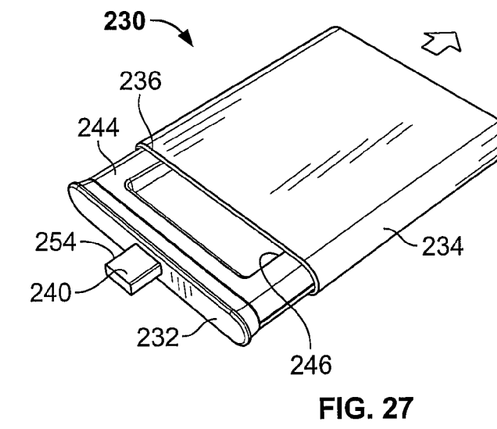
FIG. 27 is an isometric view of the dispenser of FIG. 26 in a partially open position.
Figures 28, 29:
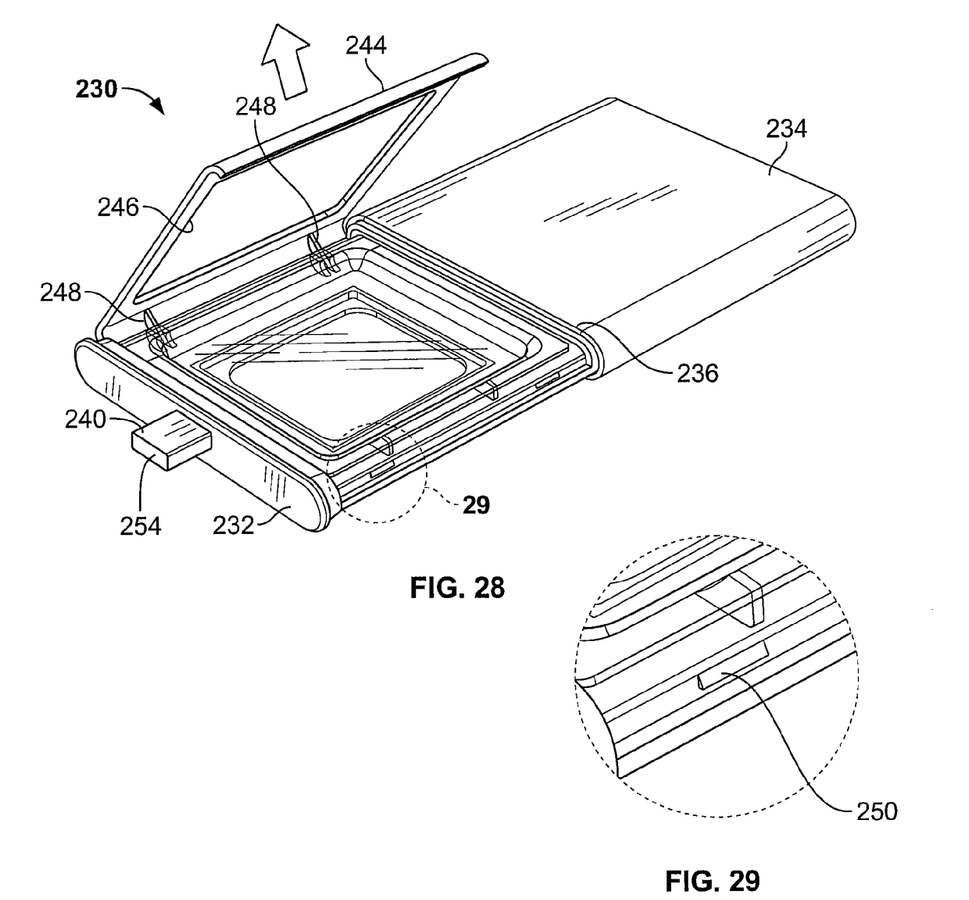
FIG. 28 is an isometric view of the dispenser of FIG. 26 in a fully open position.
FIG. 29 illustrates an enlarged portion of FIG. 28.
Figure 30:
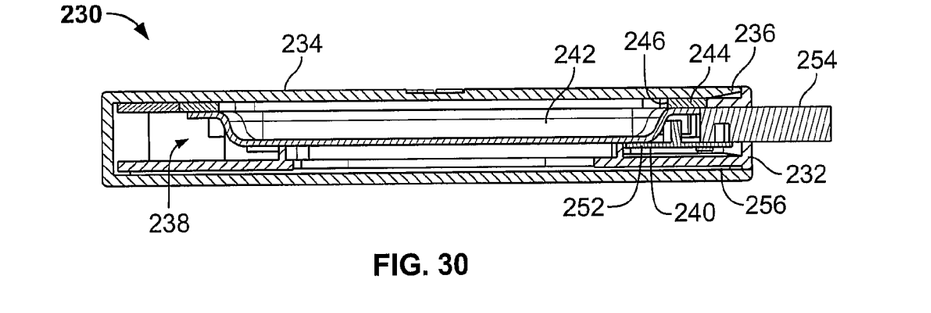
FIG. 30 is a cross-sectional view taken generally along lines 30-30 of FIG. 26.

FIGS. 21-25 illustrate another fragrance dispenser 180 that includes a clamshell housing 182 having a top portion 184 and a bottom portion 186 that are connected to one another by hinges 188. FIG. 25 shows a PCB assembly 190 that is disposed within the bottom portion 186 and is coupled to an electrical connection 192, such as a USB connector, through which the dispenser 180 receives power. The PCB assembly 190 includes one or more heating elements 194 that are energized during an active mode of operation, as described herein.

Figures 21, 22, 23, 24:
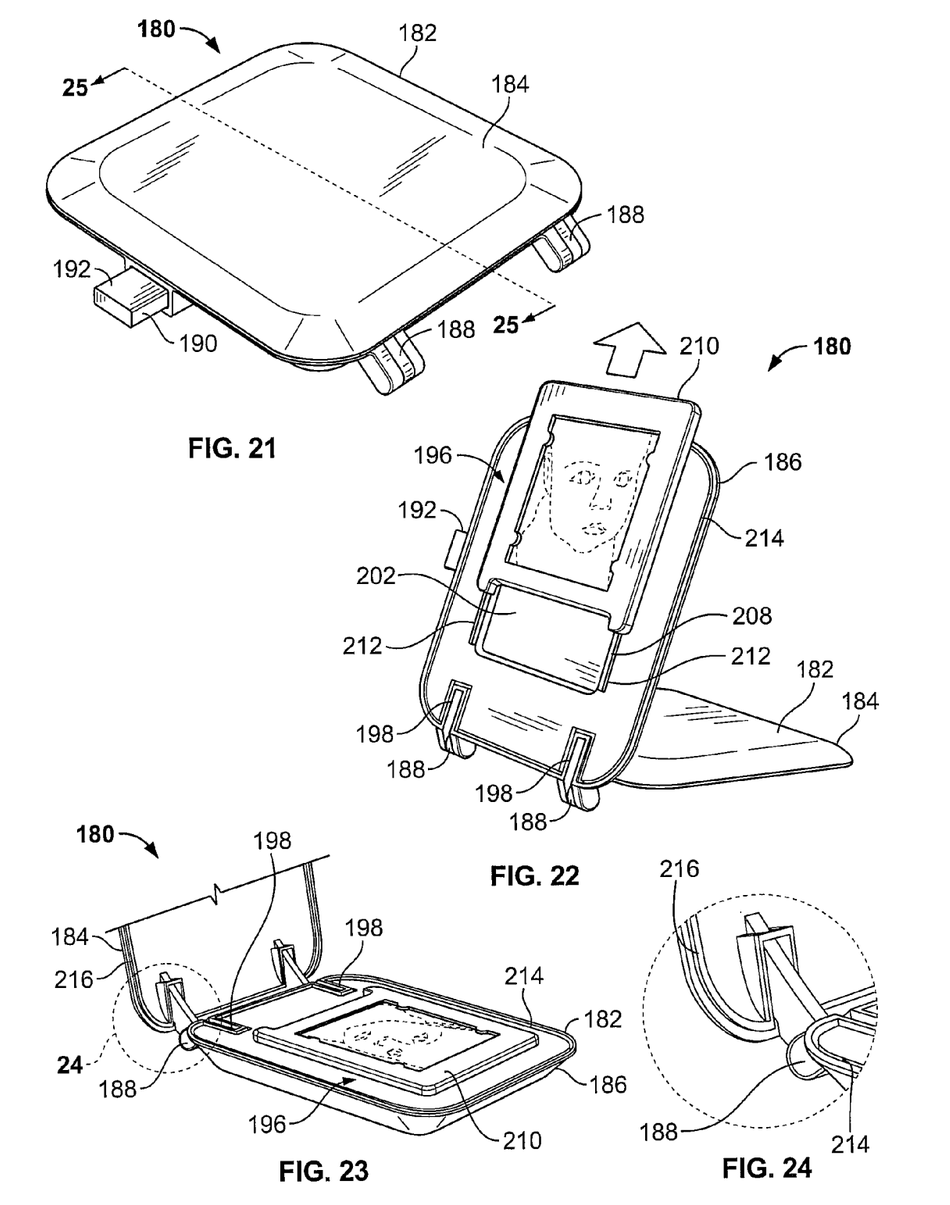
FIG. 21 is an isometric view of a dispenser according to yet another embodiment in a closed position.
FIG. 22 is an isometric view of the dispenser of FIG. 21 in a fully open position.
FIG. 23 is a partial isometric view of the dispenser of FIG. 21 in a partially open position.
FIG. 24 illustrates an enlarged portion of FIG. 23.

Referring more specifically to FIG. 22, the clamshell housing 182 is opened by rotating the bottom portion 186 about the hinges 188 to form a stand. Further, a picture frame assembly 196 is attached to the bottom portion 186 via hinges 198. The picture frame assembly 196 rotates about the hinges 198 away from the bottom portion 186 to provide access to a cavity 200 within the bottom portion 186. The cavity 200 is adapted to receive a replaceable volatile material cartridge 202 and the PCB assembly 190. In the present example, the volatile material cartridge 202 includes an impermeable cup-shaped structure 204 and a permeable membrane 206 over the cup-shaped structure 204 that acts as a sealed reservoir to contain a volatile material. The cup-shaped structure 206 is disposed adjacent the PCB assembly 190 and the permeable membrane 206 is disposed adjacent an opening 208 in the picture frame assembly 196. In one example, the volatile material cartridge 202 is similar or identical to those described in U.S. Pat. No. 7,213,770. The picture frame assembly 196 further includes a picture frame 210 that is mounted slidingly over the opening 208 on tracks 212. The picture frame 210 is moved between a closed position and an open position to vary the exposure of the opening 208 to the environment and control the intensity of the diffusion of the volatile material. In the present embodiment, the picture frame 210 can also include a magnet (not shown), which functions similarly to the magnet 148 of the volatile material dispenser 100.

FIGS. 23 and 24 illustrate a groove 214 that is defined between the picture frame assembly 196 and the bottom portion 186 of the housing 180. The top portion 182 of the housing 182 includes a gasket 216 that fits into the groove 214 to substantially prevent diffusion of the volatile material when the dispenser 180 is in the closed position of FIG. 21.

In use, the dispenser 180 can be operated in an active mode or a passive mode. In the passive mode, the electrical connection 192 is not coupled to a power source and the volatile material is allowed to diffuse passively through the opening 208 to create a desired ambient effect. The picture frame 210 is moved with respect to the opening 208 to adjust the intensity of the volatile material that is dispersed in the environment. In the active mode, the electrical connection 192 is coupled to a power source, either directly or via a cable (not shown), and the heating element(s) 194 are energized to heat and actively vaporize the volatile material within the cartridge 202 and disperse the vaporized material through the opening 208 and into the environment. In the active mode, the picture frame 210 is moved with respect to the opening 208 to adjust the intensity of the volatile material that is dispersed in the environment. Further, the PCB assembly 190 can include an LED (not shown) that is energized to provide an indication that the dispenser 180 is in the active mode of operation.

FIGS. 26-30 show another fragrance dispenser 230 that includes a housing 232 and a case 234. The case 234 has an open end 236 that slides over the housing 232. The housing 232 includes a cavity 238 that receives a PCB assembly 240 and a volatile material cartridge 242. A lid 244 with an opening 246 therethrough is attached to the housing 232 via hinges 248. The lid 244 is rotated away from the housing 232 about the hinges 248 to provide access to the cavity 238. The housing 232 further includes a catch 250 to secure the lid 244 in a closed position. The PCB assembly 240 and the volatile material cartridge 242 are similar or identical to the PCB assemblies and cartridges described hereinabove. For example, the PCB assembly 240 includes one or more heating elements 252, an electrical connection 254, and, optionally, one or more LED's (not shown). Further, the housing 232 includes a gasket 256 proximate the electrical connection 254 that forms a seal with the case 234 to substantially prevent the diffusion of the volatile material when the dispenser 230 is in a closed position (see FIG. 26).

In use, the dispenser 230 can be operated in an active mode or a passive mode. Moving the case 234 with respect to the housing 232 allows a user to adjust the intensity of the diffusion. In the passive mode the electrical connection 254 is not coupled to a power source and the volatile material is allowed to diffuse passively through the opening 246 to create a desired ambient effect. In the active mode, the electrical connection 254 is coupled to a power source and the heating element(s) 252 are energized to heat and actively vaporize the volatile material within the cartridge 242 and disperse the vaporized material through the opening 246 and into the environment. Further, the PCB assembly 240 can include one or more LED's (not shown) that are energized to provide an indication that the dispenser 130 is in the active mode of operation.

Other embodiments that include all of the possible different and various combinations of the individual features of each of the foregoing described examples are specifically included herein.

INDUSTRIAL APPLICABILITY

The volatile material dispensers disclosed herein are relatively low cost, convenient dispensers that are adapted to function as passive devices and active devices. The dispensers can also include an adjustment feature to adjust the intensity of the volatile material that is dispensed into an environment during both passive and active operation.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A volatile material dispenser, comprising:
an upper housing with an opening extending therethrough;
a lower housing with an opening extending therethrough, wherein the upper housing is secured to the lower housing to define a cavity therebetween;
electrical circuitry disposed within the cavity, wherein the electrical circuitry includes a heater and a USB interface that extends from the upper and lower housings;
a volatile material cartridge disposed within the cavity, and
a sleeve that is adapted to protect the USB interface and provide an intensity adjustment feature,
wherein the dispenser is adapted to dispense volatile material from the volatile material cartridge through the openings in the upper and lower housings in a passive mode and an active mode, and wherein the USB interface is coupled to a power source to energize the heater in the active mode.

2. The volatile material dispenser of claim 1, wherein the electrical circuitry further includes a light source that is illuminated during operation in the active mode.

3. The volatile material dispenser of claim 1, wherein the upper housing further includes a plurality of pins that interact with a plurality of openings defined by the lower housing to secure the upper and lower housings together, and wherein the lower housing includes one or more posts that define a channel that is adapted to receive the electrical circuitry, and further wherein the lower housing includes a protrusion that extends therefrom, and wherein the USB interface is disposed within the protrusion.

4. The volatile material dispenser of claim 1, wherein the electrical circuitry includes multiple heaters that are disposed around the volatile material cartridge.

5. The volatile material dispenser of claim 1, further comprising a guidance feature disposed on one or both of the upper or lower housings to orient the dispenser so that it is coupled properly to a power source.

6. The volatile material dispenser of claim 1, wherein the USB interface is adapted to be coupled to a power source in multiple orientations.

* * * * *